United States Patent [19]

Wampler

[11] Patent Number: 4,817,586
[45] Date of Patent: Apr. 4, 1989

[54] PERCUTANEOUS BLOOM PUMP WITH MIXED-FLOW OUTPUT

[75] Inventor: Richard K. Wampler, Gold River, Calif.

[73] Assignee: Nimbus Medical, Inc., Rancho Cordova, Calif.

[21] Appl. No.: 124,560

[22] Filed: Nov. 24, 1987

[51] Int. Cl.⁴ ............................................... A61F 1/24
[52] U.S. Cl. ..................................... 600/16; 604/151; 604/264; 415/DIG. 4; 415/212
[58] Field of Search .................. 128/1 D, DIG. 3; 604/151, 264; 415/212 A, 213 C, 74, DIG. 4, 198.1, 199.4, 199.6, 210, 175, 170 A

[56] References Cited

U.S. PATENT DOCUMENTS

| | | | |
|---|---|---|---|
| 4,589,822 | 5/1986 | Clausen | 415/DIG. 4 |
| 4,625,712 | 12/1986 | Wampler | 128/1 D |
| 4,688,998 | 8/1987 | Olsen | 128/1 D |
| 4,704,121 | 11/1987 | Moise | 623/3 |

Primary Examiner—Alan Cohan
Attorney, Agent, or Firm—Weissenberger & Peterson

[57] ABSTRACT

The outside diameter of an intravascular axial flow blood pump is reduced without reducing the size of its journal bearings by causing the pumped blood stream to exit through apertures in the cylindrical outside wall of the pump housing between the rotor blades and the rotor journal. This allows the journal to have a diameter of the housing, without the need for a space-consuming blood flow path around the journal.

6 Claims, 1 Drawing Sheet

PERCUTANEOUS BLOOM PUMP WITH MIXED-FLOW OUTPUT

FIELD OF THE INVENTION

This invention relates to intravascular blood pumps, and particularly to a miniature axial flow pump with a mixed radial and axial outflow pattern.

BACKGROUND OF THE INVENTION

U.S. Pat. No. 4,625,712 and copending application Ser. No. 124,874, filed Nov. 24, 1987 and entitled SINGLE-STAGE AXIAL FLOW BLOOD PUMP disclose intravascular axial flow blood pumps. Inasmuch as such pumps must be percutaneously inserted and threaded through an artery into the vicinity of the heart, it is physiologically desirable to make them as small as possible; yet in order to maintain a given blood flow, the smaller the pump, the higher its rotational speed must be. This objective, however, is restricted by practical limitations on the miniaturization of the bearings, which must have a certain minimum diameter in order to function reliably. Consequently, it has not previously been possible to construct blood pumps of this type with an outside diameter sustantially smaller than 7 mm, which is physiologically acceptable but not ideal because it would be highly desirable to make the pump fit through conventional 14-french (4.7 mm) ID percutaneous introducers.

SUMMARY OF THE INVENTION

The present invention makes it possible to construct an intravascular axial flow blood pump which has an outside diameter substantially smaller than prior art pumps, yet has bearings of the same size.

The invention accomplishes this by discharging the pumped blood not axially through the downstream end of the pump's cylindrical housing, but at an angle through elongated slots located near the center of the housing. This construction makes it possible to use the full inner diameter of the housing for the rotor journals without having to leave room for a blood path and stator blades around the journals.

It is therefore the object of the invention to provide a miniaturized axial-flow intravascular blood pump in which the space available for bearings is maximized by discharging the pumped blood partially radially and partially axially through openings formed in the pump's cylindrical housing upstream of the bearings.

DESCRIPTION OF THE PREFERRED EMBODIMENT

Figure 1:
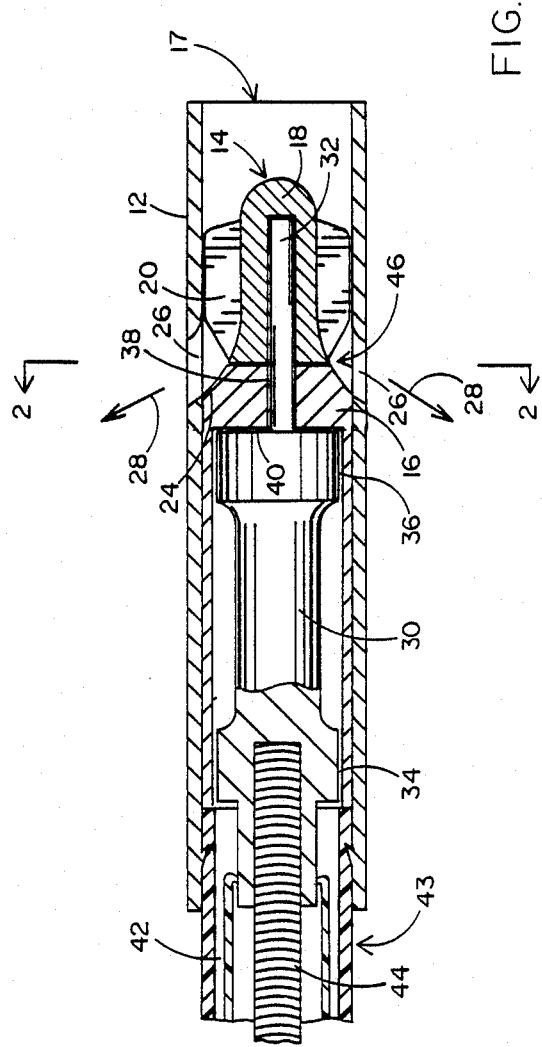
FIG. 1 is an axial section of the blood pump of this invention.
Figure 2:
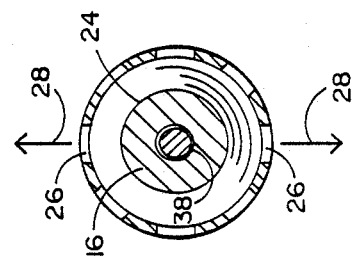
FIG. 2 is a section along line 2—2 of FIG. 1.

In FIG. 1, the blood pump of this invention is generally shown at 10. The pump 10 is contained within a cylindrical housing 12 and includes a rotor 14 and a stator 16. The housing 12 has a blood intake opening 17. The rotor 14 has a narrow, elongated hub 18. The hub 18 preferably carries a set of rotor blades 20. The hub 18 increases in diameter in the downstream direction so that the blood flow in the area of the rotor blades 20 is in a mixed axial and radial direction.

The radial component of the blood flow produced by rotor 14 is enhanced by the curvature of the deflection surface 24 of stator 16, so that the blood is propelled outwardly of the housing 12 through openings 26 in the housing wall in the general direction of arrows 28.

This construction makes it possible to use the entire inner diameter of housing 12 to house the journal 30 of the rotor shaft 32. The journal bearings 34, 36, 38 and the thrust bearing 40 are preferably of the purged-seal hydrodynamic type. Fluid for these bearings is supplied from an outside source (not shown) through the outer lumen 42 of cable sheath 43 which contains the rotor drive cable 44. The details of the construction of cable sheath 43 are described in copending application Ser. No. 124,874 and are not material to this invention. The cross section, number and shape of the openings 26 should be such as to avoid as much as possible any impediment to the blood flow, and to avoid any hemolysis-producing or thrombogenic turbulence, while maintaining the structural integrity of the housing 12. Their specific optimum geometry depends in large measure on the design of the rotor blades 20 and on the curvature of the stator surface 24 in any particular application.

The rotor hub 18 is preferably firmly but removably attached to the rotor shaft 32 by any conventional means such as screwthreads to facilitate assembly and disassembly of the pump 10 while holding it firmly together during operation.

It will be seen that the present invention provides a miniature mixed flow blood pump which can be manufactured with a substantially smaller diameter than prior art pumps of the same type, yet can accommodate a sufficiently large rotor shaft journal to provide reliability in operation, by causing the blood stream to exit the pump housing upstream of the journal bearings.

I claim:

1. An intravascular axial flow blood pump, comprising;
   (a) an elongated substantially tubular housing of substantially constant diameter having a blood intake at one end thereof;
   (b) a rotor disposed in said housing adjacent said one end, said rotor including
      (i) a hub carrying rotor blades and having a diameter substantially smaller than the inside diameter of said housing;
      (ii) a journal positioned adjacent the other end of said housing and having a diameter substantially equal to the inside diameter of said housing; and
      (iii) drive means associated with said journal for driving said rotor; and
   (c) said housing having blood exit apertures therein disposed around the periphery thereof between said blades and said journal.

2. The blood pump of claim 1, in which the diameter of said hub increases from the intake end of said hub toward said exit apertures, whereby a partially radial flow is imparted to said blood to direct it toward said apertures.

3. An intravascular axial flow blood pump, comprising;
   (a) a generally cylindrical housing having a blood intake at one end thereof;
   (b) a rotor disposed in said housing adjacent said one end, said rotor including
      (i) a hub carrying rotor blades and having a diameter substantially smaller than the inside diameter of said housing;

(ii) a journal positioned adjacent the other end of said housing and having a diameter substantially equal to the inside diameter of said housing; and (iii) drive means associated with said rotor for driving said rotor;

(c) said housing having blood exit apertures therein between said blades and said journal;

(d) said drive means including a drive cable contained within a cable sheath.

4. The blood pump of claim 1, in which said journal is supported for rotation in hydrostatic purge-sealed bearings, the purge fluid for said bearings being discharged into said blood.

5. The blood pump of claim 4, in which said drive means include a drive cable contained within a cable sheath, and said purge fluid is supplied to said pump through said cable sheath.

6. The blood pump of claim 4, in which said purge fluid is discharged in the vicinity of said apertures.

* * * * *

UNITED STATES PATENT AND TRADEMARK OFFICE
CERTIFICATE OF CORRECTION

PATENT NO.  : 4,817,586
DATED       : 04 April 1989
INVENTOR(S) : R.K. Wampler

It is certified that error appears in the above—identified patent and that said Letters Patent is hereby corrected as shown below:

On the Title page, item [54] and column 1, line 2

In the Title:

The word "BLOOM" should read --BLOOD--;

Signed and Sealed this

Twenty-third Day of April, 1991

*Attest:*

HARRY F. MANBECK, JR.

*Attesting Officer*     *Commissioner of Patents and Trademarks*